United States Patent [19]

Wehner et al.

[11] Patent Number: 5,155,152

[45] Date of Patent: Oct. 13, 1992

[54] SUBSTITUTE AMINOPYRROLES AS STABILIZERS FOR CHLORINE-CONTAINING POLYMERS

[75] Inventors: Wolfgang Wehner, Zwingenberg; Hermann O. Wirth, Bensheim, both of Fed. Rep. of Germany

[73] Assignee: Ciba-Geigy Corporation, Ardsley, N.Y.

[21] Appl. No.: 496,380

[22] Filed: Mar. 19, 1990

[30] Foreign Application Priority Data

Mar. 28, 1989 [CH] Switzerland .................. 1117/89

[51] Int. Cl.$^5$ .................. C08K 5/34; C07D 207/32
[52] U.S. Cl. .................. 524/100; 524/104; 524/105; 544/212; 548/401; 548/531; 548/537; 548/558
[58] Field of Search .............. 524/100, 104, 105, 531; 548/558, 537, 401; 544/212

[56] References Cited

U.S. PATENT DOCUMENTS

| | | | |
|---|---|---|---|
| 3,993,650 | 1/1976 | Tarzia et al. | 260/256.4 |
| 4,088,773 | 5/1978 | Evans et al. | 548/558 |
| 4,097,481 | 6/1978 | Banitt et al. | 548/558 |
| 4,140,696 | 2/1979 | Tarzia et al. | 260/326.5 |
| 4,198,502 | 4/1980 | Tarzia et al. | 542/414 |
| 4,211,708 | 7/1980 | Tarzia et al. | 260/326.46 |
| 4,211,709 | 7/1980 | Tarzia et al. | 260/326.47 |
| 4,212,806 | 7/1980 | Tarzia et al. | 260/326.2 |
| 4,290,940 | 9/1981 | Wirth et al. | 260/45.8 |
| 4,369,276 | 1/1983 | Wirth et al. | 524/104 |

FOREIGN PATENT DOCUMENTS 0022087  1/1981  European Pat. Off.
2439284  8/1973  Fed. Rep. of Germany.

OTHER PUBLICATIONS

E. Toja, J. Hetero. Chem., 23, 1561 (1986).
J. R. Ross, J. Hetero. Chem. 22, 817 (1985).
S. M. Bayomi, J. Hetero. Chem. 22, 83 (1985).

*Primary Examiner*—Kriellion S. Morgan
*Attorney, Agent, or Firm*—JoAnn Villamizar; William A. Teoli, Jr.

[57] ABSTRACT

The compounds of formula I

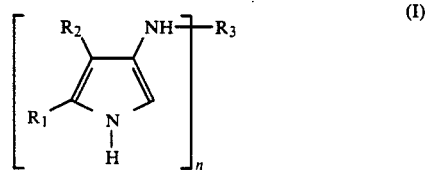

wherein n is 1 or 2, $R_1$ is $C_1$-$C_4$alkyl, $R_2$ and $R_3$ are, for example, alkanoyl or alkanoyloxy or $R_3$ may also be, for example, alkanedioyl, are suitable for stabilizing chlorine-containing polymers against thermal and light-induced degradation.

Some of the compounds of formula I are novel.

18 Claims, No Drawings

SUBSTITUTE AMINOPYRROLES AS STABILIZERS FOR CHLORINE-CONTAINING POLYMERS

The present invention relates to chlorine-containing polymers containing aminopyrroles, to the use of the aminopyrrole compounds for stabilising chlorine-containing polymers against thermal and light-induced degradation, and to novel aminopyrroles.

It is known that chlorine-containing polymers have to be protected from the damaging effect of light and heat, especially in processing to preforms. The use of pyrroles as stabilisers for chlorine-containing thermoplastics is described, for example, in EP-A-22087.

The preparation of substituted aminopyrroles is described, for example, in the following publications: E. Toja et al., J. Heterocyclic Chem. 23, 1561 (1986); J. R. Ross et al., J. Heterocyclic Chem. 22, 817 (1985); S. M. Bayomi et al., J. Heterocyclic Chem. 22, 83 (1985).

The use of aminopyrroles as medicaments is described, for example, in U.S. Pat. No. 3,993,650 and DE-A-2 439 284.

The present invention relates to compositions containing a) a chlorine-containing polymer and b) at least one compound of formula I

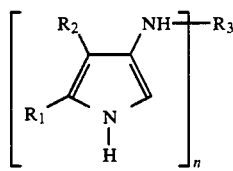

wherein n is 1 or 2, $R_1$ is $C_1$-$C_4$alkyl, $R_2$ is a group of formula IIa, IIb, IIc or IId

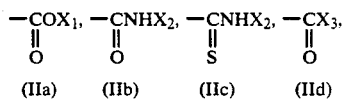

$X_1$ is hydrogen, $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, hydroxy, methoxy or/and by ethoxy, $C_7$-$C_{10}$phenylalkyl or $C_7$-$C_{10}$phenylalkyl substituted in the phenyl radical by $C_1$-$C_{20}$alkyl, chlorine, hydroxy, methoxy or/and by ethoxy, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is a group of formula IIIa to IIIg

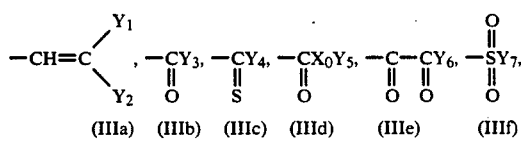

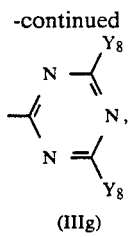

$X_0$ is an oxygen atom or a sulfur atom, $Y_1$ and $Y_2$ are each independently of the other —CN, benzoyl, $C_2$-$C_4$alkanoyl or $C_2$-$C_4$alkoxycarbonyl, $Y_3$ is $C_1$-$C_{20}$alkyl, $C_3$-$C_{20}$alkenyl, phenyl, phenyl substituted by $C_1$-$C_4$alkyl, chlorine, —$NO_2$, methoxy or/and by ethoxy, 2-phenylethenyl, di($C_1$-$C_4$alkyl)amino, diphenylamino, $C_1$-$C_{20}$alkylamino, $C_3$-$C_8$cycloalkylamino, phenylamino, phenylamino substituted in the phenyl ring by $C_1$-$C_4$alkyl, chlorine, hydroxy, methoxy or/and by ethoxy, benzylamino, benzenesulfonamido or toluenesulfonamido, $Y_4$ is di($C_1$-$C_4$alkyl)amino, diphenylamino, $C_1$-$C_8$alkylamino, phenylamino, phenylamino substituted in the phenyl ring by $C_1$-$C_4$alkyl, chlorine, hydroxy, methoxy or/and by ethoxy, or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, $C_7$-$C_{10}$phenylalkyl or $C_7$-$C_{10}$phenylalkyl substituted in the phenyl radical by $C_1$-$C_{20}$alkyl, $Y_6$ is $C_1$-$C_4$alkoxy, phenylamino or phenylamino substituted in the phenyl group by $C_1$-$C_4$alkyl, chlorine, hydroxy, methoxy or/and by ethoxy, $Y_7$ is $C_1$-$C_4$alkyl, phenyl or phenyl substituted by $C_1$-$C_4$alkyl, chlorine, —$NO_2$, ($C_1$-$C_{12}$alkyl)oxycarbonyl and/or by phenoxycarbonyl, the radicals $Y_8$ are each independently of the other $C_1$-$C_4$alkoxy or allyloxy, and when n is 2 $R_3$ is a group of formula IVa, IVb, IVc or IVd

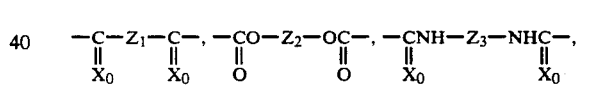

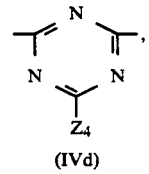

$X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

Alkyl having up to 20 carbon atoms is, for example, methyl, ethyl, propyl, butyl, tert.-butyl, pentyl, hexyl, heptyl, octyl, isooctyl, isononyl, decyl, dodecyl or octadecyl.

$R_1$ is preferably straight-chain $C_1$-$C_4$alkyl, especially methyl.

A preferred meaning of $X_1$ is $C_1$-$C_{18}$alkyl, especially $C_1$-$C_{12}$alkyl, for example methyl or ethyl.

$X_3$ as alkyl is preferably methyl or ethyl, especially methyl.

$Y_5$ as alkyl preferably has from 1 to 4 carbon atoms. Methyl and ethyl are especially preferred meanings of $Y_5$.

$C_1$-$C_4$alkoxy is, for example, methoxy, ethoxy, propoxy or butoxy.

$C_3$-$C_6$alkyl interrupted by 1 or 2 oxygen atoms is, for example, 3-oxabutyl, 3-oxapentyl, 3-oxaheptyl, 3,6-dioxaheptyl or 3,6-dioxaoctyl.

$C_3$-$C_6$alkyl interrupted by 1 or 2 oxygen atoms or sulfur atoms or/and substituted by OH may be, for example, in addition to the radicals mentioned in the preceding paragraph, 3-thiabutyl, 3-thiapentyl, 3,6-dithiaheptyl, 3,6-dithiaoctyl, 5-hydroxy-3-oxapentyl, 5-hydroxy-3-thiapentyl or 4-hydroxybutyl.

$C_3$-$C_{20}$alkenyl is, for example, allyl, 2-methallyl, 3-methylbut-2-enyl, 3-methylbut-3-enyl, hexenyl, decenyl, undecenyl, heptadecenyl or oleyl. Preferred meanings are allyl, methallyl and oleyl.

$C_5$-$C_{12}$cycloalkyl which may be unsubstituted or substituted by $C_1$-$C_4$alkyl, especially methyl, is, for example, cyclopentyl, cyclohexyl, cycloheptyl, cyclooctyl, cyclodecyl, cyclododecyl or methylcyclohexyl. Unsubstituted or substituted $C_5$-$C_8$cycloalkyl, especially cyclohexyl, is preferred.

Examples of phenyl substituted by, preferably from 1 to 3, radicals in accordance with the definition are o-, m- or p-chlorophenyl, 2,3-dichlorophenyl, 2,4-dichlorophenyl, 2,5-dichlorophenyl, 2,6-dichlorophenyl, 3,4-dichlorophenyl, 2,4,5-trichlorophenyl, 2,4,6-trichlorophenyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 2-methyl-4-tert.-butylphenyl, 2-ethylphenyl, 2,6-diethylphenyl, 2,6-diethyl-4-methylphenyl, 2,6-diisopropylphenyl, 4-tert.-butylphenyl, p-nonylphenyl, 2-chloro-6-methylphenyl, 3-chloro-2-methylphenyl, 3-chloro-4-methylphenyl, 4-chloro-2-methylphenyl, 5-chloro-2-methylphenyl, 2,6-dichloro-3-methylphenyl, o-, m- or p-methoxyphenyl, o- or p-ethoxyphenyl, 2,4-dimethoxyphenyl, 2,5-dimethoxyphenyl, 2,5-diethoxyphenyl, 2-methoxy-5-methylphenyl, 4-methoxy-2-methylphenyl, 3-chloro-4-methoxyphenyl, 3-chloro-6-methoxyphenyl, 3-chloro-4,6-dimethoxyphenyl, 4-chloro-2,5-dimethoxyphenyl, o-, m- or p-hydroxyphenyl, 2-hydroxy-4-methylphenyl, 3-hydroxy-4-methylphenyl, o-, m- or p-acetylaminophenyl, o-, m- or p-nitrophenyl, p-($C_1$-$C_{12}$alkyl)oxycarbonylphenyl and p-phenoxycarbonylphenyl.

When $Y_3$, $Y_4$ and $Y_6$ are phenylamino substituted in the phenyl radical by, preferably from 1 to 3, radicals in accordance with the definition, the substituted phenyl radical may have, for example, the meanings given above.

$C_7$-$C_{10}$phenylalkyl is, for example, benzyl or 2-phenylethyl. Benzyl is preferred. When the phenyl group in these radicals is substituted by, preferably from 1 to 3, groups in accordance with the definition, it may have the meanings given above. $C_7$-$C_{10}$phenylalkyl substituted in the phenyl group by $C_1$-$C_{20}$alkyl, preferably $C_8$-$C_{14}$alkyl, is one of the preferred meanings. Dodecylbenzyl is also to be mentioned as an example.

$C_2$-$C_4$alkanoyl is, for example, acetyl, propanoyl or butanoyl. Acetyl is preferred.

$C_2$-$C_4$alkoxycarbonyl is, for example, methoxycarbonyl, ethoxycarbonyl or propoxycarbonyl. Methoxycarbonyl and ethoxycarbonyl are preferred.

Di($C_1$-$C_4$alkyl)amino is, for example, dimethylamino, diethylamino, dipropylamino or dibutylamino.

$C_1$-$C_{20}$alkylamino, preferably $C_1$-$C_8$alkylamino, especially $C_4$-$C_8$alkylamino, is, for example, butylamino, pentylamino, hexylamino, heptylamino or octylamino.

$C_3$-$C_8$cycloalkylamino is, for example, cyclopropylamino, cyclohexylamino or cyclooctylamino.

Alkylene having up to 12 carbon atoms is, for example, methylene, dimethylene, trimethylene, butylene, pentamethylene, hexamethylene, octamethylene, decamethylene or dodecamethylene. Alkylene having up to 8 carbon atoms is preferred.

Of interest are compositions wherein n is 1 or 2, $R_1$ is $C_1$-$C_4$alkyl, $R_2$ is a group of formula IIa, IIb, IIc or IId, $X_1$ is $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_1$-$C_{20}$alkyl, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is a group of formula IIIa to IIIg, $X_0$ is an oxygen atom, $Y_1$ and $Y_2$ are each independently of the other —CN, benzoyl, $C_2$-$C_4$alkanoyl or $C_2$-$C_4$alkoxycarbonyl, $Y_3$ is $C_1$-$C_{20}$alkyl, $C_3$-$C_{20}$alkenyl, phenyl, phenyl substituted by $C_1$-$C_4$alkyl, chlorine, methoxy or/and by ethoxy, 2-phenylethenyl, di($C_1$-$C_4$alkyl)amino, $C_1$-$C_8$alkylamino, phenylamino, benzylamino, benzenesulfonamido or toluenesulfonamido, $Y_4$ is di($C_1$-$C_4$alkyl)amino, $C_1$-$C_8$alkylamino, phenylamino or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, $C_7$-$C_{10}$phenylalkyl or $C_7$-$C_{10}$phenylalkyl substituted in the phenyl radical by $C_1$-$C_{20}$alkyl, $Y_6$ is $C_1$-$C_4$alkoxy, phenylamino or phenylamino substituted in the phenyl group by $C_1$-$C_4$alkyl, chlorine, methoxy or/and by ethoxy, $Y_7$ is phenyl or tolyl, the radicals $Y_8$ are each independently of the other $C_1$-$C_4$alkoxy or allyloxy, and when n is 2 $R_3$ is a group of formula IVa, IVb, IVc or IVd, $X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

Preferred are compositions wherein $X_1$ is $C_1$-$C_{18}$alkyl, $C_3$-$C_6$alkyl interrupted by one or two oxygen atoms or sulfur atoms or/and substituted by OH, allyl, methallyl, oleyl, $C_5$-$C_8$cycloalkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_8$-$C_{14}$alkyl, $X_3$ is methyl, ethyl or phenyl, $Y_3$ is $C_1$-$C_{18}$alkyl, allyl, methallyl, oleyl, phenyl, phenyl substituted by $C_1$-$C_4$alkyl, chlorine, methoxy or/and by ethoxy, 2-phenylethenyl or di($C_1$-$C_4$alkyl)amino, and $Y_5$ is $C_1$-$C_{18}$alkyl, $C_5$-$C_8$cycloalkyl, phenyl, $C_7$-$C_{10}$phenylalkyl or $C_7$-$C_{10}$phenylalkyl substituted in the phenyl radical by $C_8$-$C_{14}$alkyl.

Also preferred are compositions wherein n is 1, $R_2$ is a group of formula IIa or IIc, and $R_3$ is a group of formula IIIb, IIId or IIIg.

The radical $R_3$ is preferably a group of formula IIIb, IIId or IIIg.

Especially preferred are compositions wherein n is 1, $R_1$ is methyl, $R_2$ is a group of formula IIa, $X_1$ is $C_1$-$C_{12}$alkyl, $R_3$ is a group of formula IIIb, IIId, or IIIg, $Y_3$ is $C_1$–$C_{18}$alkyl, allyl, phenyl or phenyl substituted by $C_1$–$C_4$alkyl, chlorine, methoxy or/and by ethoxy, and $Y_5$ is $C_1$–$C_{18}$alkyl, cyclohexyl, phenyl or benzyl.

Compositions wherein n is 1, $R_1$ is methyl, $R_2$ is a group of formula IIa, $X_1$ is $C_1$–$C_4$alkyl, especially methyl or ethyl, $R_3$ is a group of formula IIId, and $Y_5$ is methyl, ethyl or phenyl are a further preferred embodiment of the invention.

Those compositions wherein $R_3$ is a group of formula IIIg are also preferred.

According to a further preferred embodiment, n is 2.

There are also of interest those compositions wherein n is 2 and $R_3$ is a group of formula IVa or IVb.

$R_2$ is most preferably a group of formula IIa.

Preferred examples of compounds of formula I are:
2-methyl-3-methoxycarbonyl-4-ethoxycarbonylaminopyrrole,
2-methyl-3-methoxycarbonyl-4-methoxycarbonylaminopyrrole,
2-methyl-3-ethoxycarbonyl-4-ethoxycarbonylaminopyrrole,
2-methyl-3-ethoxycarbonyl-4-methoxycarbonylaminopyrrole,
2-methyl-3-methoxycarbonyl-4-benzoylaminopyrrole,
2-methyl-3-ethoxycarbonyl-4-benzoylaminopyrrole,
2-methyl-3-methoxycarbonyl-4-(2',4'-diallyloxy-1',3',5'-triazin-6'-yl)aminopyrrole,
2-methyl-3-methoxycarbonyl-4-[benzyl(thiocarbonyl)]aminopyrrole,
1,4-bis[(2'-methyl-3'-methoxycarbonylpyrrol-4'-yl)carbamoyloxy]butane,
1,6-bis[(2'-methyl-3'-methoxycarbonylpyrrol-4'-yl)carbamoyloxy]hexane,
1,5-bis[(2'-methyl-3'-methoxycarbonylpyrrol-4'-yl)carbamoyloxy]-3-oxapentane,
1,4-bis[(2'-methyl-3'-methoxycarbonylpyrrol-4'-yl)carbamoyl]butane,
1,5-bis[(2'-methyl-3'-methoxycarbonylpyrrol-4'-yl)carbamoyl]pentane,
1,6-bis[(2'-methyl-3'-methoxycarbonylpyrrol-4'-yl)carbamoyl]hexane,
1,7-bis[(2'-methyl-3'-methoxycarbonylpyrrol-4'-yl)carbamoyl]heptane,
1,8-bis[(2'-methyl-3'-methoxycarbonylpyrrol-4'-yl)carbamoyl]octane,
1,4-bis[(2'-methyl-3'-methoxycarbonylpyrrol-4'-yl)carbamoyl]benzene,
1,4-bis[(2'-methyl-3'-methoxycarbonylpyrrol-4'-yl)aminothiocarbonyl]butane,
1,5-bis[(2'-methyl-3'-methoxycarbonylpyrrol-4'-yl)aminothiocarbonyl]pentane,
1,6-bis[(2'-methyl-3'-methoxycarbonylpyrrol-4'-yl)aminothiocarbonyl]hexane,
1,7-bis[(2'-methyl-3'-methoxycarbonylpyrrol-4'-yl)aminothiocarbonyl]heptane,
1,8-bis[(2'-methyl-3'-methoxycarbonylpyrrol-4'-yl)aminothiocarbonyl]octane,
1,4-bis[(2'-methyl-3'-methoxycarbonylpyrrol-4'-yl)aminothiocarbonyl]benzene.

The compound 2-methyl-3-methoxycarbonyl-4-ethoxycarbonylaminopyrrole, 2-methyl-3-methoxycarbonyl-4-benzoylaminopyrrole, 2-methyl-3-methoxycarbonyl-4-(2',4'-diallyloxy-1',3',5'-triazin-6'-yl)aminopyrrole, 1,4-bis[(2'-methyl-3'-methoxycarbonylpyrrol-4'-yl)carbamoyl]butane or 1,6-bis[(2'-methyl-3'-methoxycarbonylpyrrol-4'-yl)carbamoyloxy]hexane is most preferably used in the compositions of the invention.

The chlorine-containing polymers are preferably vinyl chloride homopolymers or copolymers. Suitable comonomers for the copolymers are, for example: vinyl acetate, vinylidene chloride, transdichloroethene, ethylene, propylene, butylene, maleic acid, acrylic acid, fumaric acid, itaconic acid. Other suitable chlorine-containing polymers are postchlorinated PVC and chlorinated polyolefins, and also graft polymers of PVC with EVA, ABS and MBS. Preferred substrates are also mixtures of the above-mentioned homopolymers and copolymers, especially vinyl chloride homopolymers, with other thermoplastic or/and elastomeric polymers, especially with ABS, MBS, NBR, SAN, EVA.

Also preferred are suspension polymers, bulk polymers and emulsion polymers.

Polyvinyl chloride is especially preferred as the chlorine-containing polymer.

It is advantageous to use the compounds of formula I together with known thermostabilisers, such as, for example, organotin compounds, lead compounds, organic antimony compounds, Me(II) phenolates, especially $C_7$–$C_{20}$alkyl phenolates, for example nonyl phenolate, or Me(II) carboxylates. Me(II) is, for example, Ba, Ca, Mg, Cd or Zn. The carboxylates are preferably salts of carboxylic acids having from 7 to 20 carbon atoms, for example benzoates, alkenoates or alkanoates, preferably stearates, oleates, laurates, palmitates, hydroxystearates or 2-ethylhexanoates. Stearates, oleates and p-tert.-butyl benzoates are especially preferred. Examples of organotin compounds, lead compounds and organic antimony compounds are the compounds mentioned in U.S. Pat. No. 4,743,640, column 3, line 48 to column 5, line 38.

In addition, the chlorine-containing polymers stabilised with the compounds of formula I may contain conventional PVC-stabilisers in customary amounts, such as, for example, phosphites or epoxy compounds.

The phosphites are preferably those of the formulae

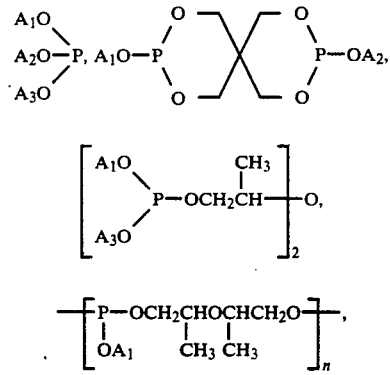

wherein $A_1$, $A_2$ and $A_3$ are each independently of the others $C_4$–$C_{18}$alkyl, $C_6$–$C_{18}$alkenyl, $C_5$–$C_7$cycloalkyl, phenyl or phenyl substituted by from one to three $C_1$–$C_{12}$alkyl groups.

Examples are trioctyl, tridecyl, tridodecyl, tritetradecyl, tristearyl, trioleyl, triphenyl, tricresyl, tris-p-nonylphenyl and tricyclohexyl phosphite. Preferred are the aryldialkyl and alkyldiaryl phosphites, such as for example, phenyldidecyl, (2,4-di-tert.-butylphenyl)didodecyl, (2,6-di-tert.-butylphenyl)didodecyl phosphite and the dialkyl and diaryl pentaerythritol diphosphites, such as, for example, distearyl pentaerythritol diphosphite. Also preferred are the tetraphenyl- and tetraalkyl-[dipropylene glycol-1,2]diphosphites and the poly-[dipropylene glycol-1,2-phenyl phosphites] and the poly-[dipropylene glycol-1,2-alkyl phosphites].

Especially preferred organic phosphites are distearyl pentaerythritol diphosphite, tris(nonylphenyl) phosphite, phenyldidecyl phosphite, tetraphenyl-[dipropylene glycol-1,2] diphosphite and poly-[dipropylene glycol-1,2-phenyl phosphite].

The epoxy compounds are preferably epoxidised oils and epoxidised fatty acid esters, for example epoxidised soybean oil, epoxidised butyl oleate and epoxidised octyl oleate.

The invention therefore relates preferably also to compositions containing, in addition to component a) and a compound of formula I, at least one Me(II) carboxylate and/or Me(II) phenolate wherein Me(II) is Ba, Ca, Mg, Cd or Zn.

In accordance with a further preference, the compositions of the invention contain, in addition to component a) and a compound of formula I, at least one Me(II) carboxylate wherein Me(II) is Ba, Ca, Mg or Zn. Mixtures of Ba/Zn carboxylates or Ca/Zn carboxylates are especially preferred as co-stabilisers.

Also preferred are compositions containing, in addition to component a) and a compound of formula I, an epoxy compound and/or a phosphite and optionally an Me(II) carboxylate and/or Me(II) phenolate.

The known thermostabilisers (e.g. carboxylates) may be present in the material to be stabilised in a concentration known to the skilled person, such as, for example, in amounts of from 0.05 to 5% by weight.

The phosphites are employed, for example, in concentrations of from 0.3 to 5, preferably from 0.5 to 1, % by weight, and the epoxy compounds, such as, for example, epoxidised soybean oil, advantageously in concentrations of from 1 to 8, preferably from 1 to 3, % by weight.

The compounds of formula I are incorporated into the chlorine-containing polymer, for example, in amounts of from 0.05 to 5, preferably from 0.05 to 1, especially from 0.1 to 0.5, % by weight.

% by weight data refer in each case to the material to be stabilised.

Depending on the intended use of the polymers, other additives, such as, for example, phenolic antioxidants, lubricants (preferably montan waxes or glycerol esters), fatty acid esters, paraffins, plasticisers, fillers, carbon black, asbestos, kaolin, talc, glass fibres, modifiers (such as impact resistance additives), optical brighteners, pigments, light-stabilising agents, UV-absorbers, flame retardants or antistatic agents, may be incorporated prior to or during incorporation of the stabilisers.

Other possible additives are b-aminocrotonates, e.g. the compounds described in DE-A-804 442, DE-A-807 207 and JP-A-75/17454, pyrroles, e.g. the compounds mentioned in EP-A-22 087, aminouracils, e.g. the compounds disclosed in EP-A-65 934, aminothiouracils, e.g. the compounds known from EP-A-41 479, polyols, e.g. the compounds described in DE-A-3 019 910, b-diketones, e.g. the compounds mentioned in DE-A-2 600 516, or also mixtures of b-diketones and hydrotalcites as described e.g. in EP-A-63 180.

The incorporation of the stabiliser components into the chlorine-containing polymer is carried out most advantageously, as is usual, in a roll mill, for example a 2-roll mill, at temperatures of from 150° to 200° C. Sufficient homogenisation can generally be achieved within a period of from 5 to 15 minutes. The components can be added individually or together in the form of a pre-mix. A liquid pre-mix has proved advantageous, that is to say the operation is carried out in the presence of inert solvents and/or plasticisers.

The invention further relates to the use of compounds of formula 1 for stabilising chlorine-containing polymers against thermal and light-induced degradation.

The invention also relates to the novel compounds of formula Ia

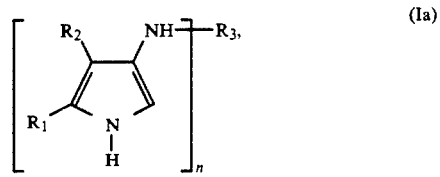

wherein n is 1 or 2, $R_1$ is $C_1$–$C_4$alkyl, $R_2$ is a group of formula IIa, IIb, IIc or IId

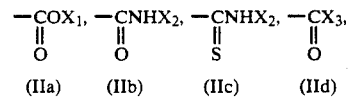

$X_1$ is hydrogen, $C_1$–$C_{20}$alkyl, $C_3$–$C_6$alkyl interrupted by one or two oxygen atoms or sulfur atoms or/and substituted by OH, $C_3$–$C_{20}$alkenyl, $C_5$–$C_{12}$cycloalkyl, $C_5$–$C_{12}$cycloalkyl substituted by $C_1$–$C_4$alkyl, phenyl, phenyl substituted by $C_1$–$C_{10}$alkyl, chlorine, hydroxy, methoxy or/and by ethoxy, $C_7$–$C_{10}$phenylalkyl or $C_7$–$C_{10}$phenylalkyl substituted in the phenyl radical by $C_1$–$C_{20}$alkyl, chlorine, hydroxy, methoxy or/and by ethoxy, $X_2$ is phenyl or phenyl substituted by from 1 to 3 radicals, the radicals being selected from the group consisting of $C_1$–$C_4$alkyl, chlorine, hydroxy, methoxy, ethoxy and acetylamino, $X_3$ is $C_1$–$C_8$alkyl or phenyl, when n is 1 $R_3$ is a group of formula IIIb to IIIg

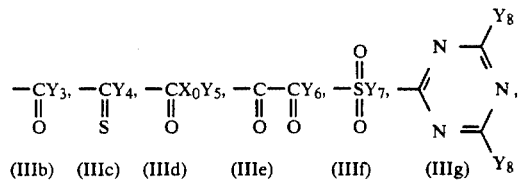

$X_0$ is an oxygen atom or a sulfur atom, $Y_3$ is $C_4$–$C_{20}$alkyl, $C_3$–$C_{20}$alkenyl, phenyl, phenyl substituted by $C_1$–$C_4$alkyl, chlorine, —$NO_2$, methoxy or/and by ethoxy, 2-phenylethenyl, di($C_1$–$C_4$alkyl)amino, diphenylamino, $C_1$–$C_{20}$alkylamino, $C_3$–$C_8$cycloalkylamino, phenylamino, phenylamino substituted in the phenyl ring by $C_1$–$C_4$alkyl, chlorine, hydroxy, methoxy or/and by ethoxy, benzylamino, benzenesulfonamido or toluenesulfonamido, $Y_4$ is di($C_1$–$C_4$alkyl)amino, diphenylamino, $C_1$–$C_8$alkylamino, phenylamino, phenylamino substituted in the phenyl ring by $C_1$–$C_4$alkyl, chlorine, hydroxy, methoxy or/and by ethoxy, or benzylamino, $Y_5$ is $C_1$–$C_{20}$alkyl, $C_3$–$C_6$alkyl interrupted by one or two oxygen atoms, $C_5$–$C_{12}$cycloalkyl, $C_5$–$C_{12}$cycloalkyl substituted by $C_1$–$C_4$alkyl, phenyl, or $C_7$–$C_{10}$phenylalkyl substituted in the phenyl radical by $C_1$–$C_{20}$alkyl, $Y_6$ is $C_1$–$C_4$alkoxy, phenylamino or phenylamino substituted in the phenyl group by $C_1$–$C_4$alkyl, chlorine, hydroxy, methoxy or/and by ethoxy, $Y_7$ is $C_1$–C-

4alkyl, phenyl or phenyl substituted by $C_1$-$C_4$alkyl, chlorine, —$NO_2$, ($C_1$-$C_{12}$alkyl)oxycarbonyl and/or by phenoxycarbonyl, the radicals $Y_8$ are each independently of the other $C_1$-$C_4$alkoxy or allyloxy, and when n is 2 $R_3$ is a group of formula IVa, IVb, IVc or IVd

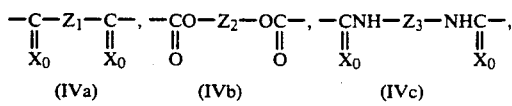

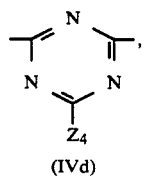

(IVd)

$X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

Preferred meanings of the variables $R_1$, $R_2$, $R_3$ and n are those specified above for formula I.

Of interest are compounds of formula Ia wherein n is 1 or 2, $R_1$ is $C_1$-$C_4$alkyl, $R_2$ is a group of formula IIa, IIb, IIc or IId, $X_1$ is $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_1$-$C_{20}$alkyl, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is a group of formula IIIb to IIIg, $X_0$ is an oxygen atom, $Y_3$ is $C_4$-$C_{20}$alkyl, $C_3$-$C_{20}$alkenyl, phenyl, phenyl substituted by $C_1$-$C_4$alkyl, chlorine, methoxy or/and by ethoxy, 2-phenylethenyl, di($C_1$-$C_4$alkyl)amino, $C_1$-$C_8$alkylamino, phenylamino, benzylamino, benzenesulfonamido or toluenesulfonamido, $Y_4$ is di($C_1$-$C_4$alkyl)amino, $C_1$-$C_8$alkylamino, phenylamino or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, or $C_7$-$C_{10}$phenylalkyl substituted in the phenyl radical by $C_1$-$C_{20}$alkyl, $Y_6$ is $C_1$-$C_4$alkoxy, phenylamino or phenylamino substituted in the phenyl group by $C_1$-$C_4$alkyl, chlorine, methoxy or/and by ethoxy, $Y_7$ is phenyl or tolyl, the radicals $Y_8$ are each independently of the other $C_1$-$C_4$alkoxy or allyloxy, and when n is 2 $R_3$ is a group of formula IVa, IVb, IVc or IVd, $X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

Also of interest are compounds of formula Ia wherein $X_1$ is $C_1$-$C_{18}$alkyl, $C_3$-$C_6$alkyl interrupted by one or two oxygen atoms or sulfur atoms or/and substituted by OH, allyl, methallyl, oleyl, $C_5$-$C_8$cycloalkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_8$-$C_{14}$alkyl, $X_3$ is methyl, ethyl or phenyl, $Y_3$ is $C_4$-$C_{18}$alkyl, allyl, methallyl, oleyl, phenyl, phenyl substituted by $C_1$-$C_4$alkyl, chlorine, methoxy or/and by ethoxy, 2-phenylethenyl or di($C_1$-$C_4$alkyl)amino, and $Y_5$ is $C_1$-$C_{18}$alkyl, $C_5$-$C_8$cycloalkyl, phenyl, or $C_7$-$C_{10}$phenylalkyl substituted in the phenyl radical by $C_8$-$C_{14}$alkyl.

2-Methyl-3-methoxycarbonyl-4-ethoxycarbonylaminopyrrole, 2-methyl-3-methoxycarbonyl-4-benzoylaminopyrrole, 2-methyl-3-methoxycarbonyl-4-(2',4'-diallyloxy-1',3',5'-triazin-6'-yl)aminopyrrole, 1,4-bis[(2'-methyl-3'-methoxycarbonylpyrrol-4'-yl)carbamoyl]butane or 1,6-bis[(2'-methyl-3'-methoxycarbonylpyrrol-4'-yl)carbamoyloxy]hexane is an especially preferred compound of formula Ia.

The compounds of formulae I and Ia may be prepared by processes analogous to known processes, for example in accordance with the scheme shown below

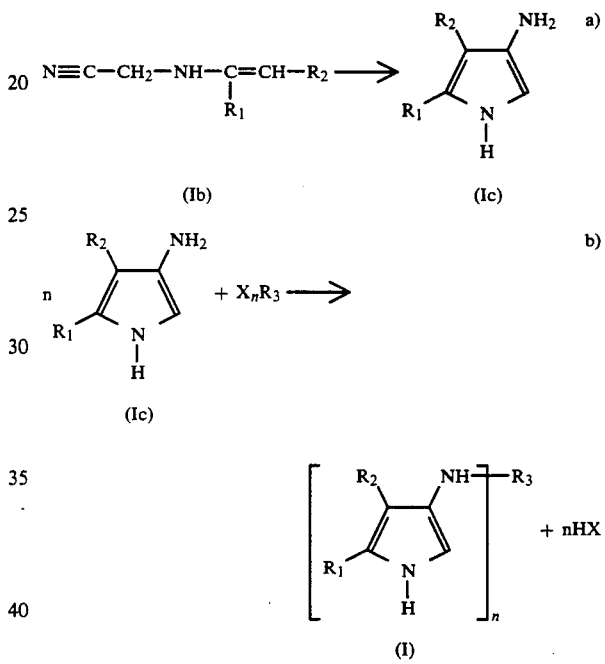

X may be, for example, halogen, preferably chlorine.

The cyclisation a) is carried out, for example, in an alkali metal alcoholate solution. It is advantageous to carry out the subsequent reaction b) in situ, that is to say without isolating the compound of formula Ic. Before carrying out reaction b) it is advantageous to neutralise the reaction mixture, for example with glacial acetic acid or aqueous mineral acids. When X is halogen, reaction b) is advantageously carried out in the presence of a hydrogen halide acceptor, such as, for example, a tertiary amine.

Some of the compounds of formulae I and Ia wherein $R_3$ is a group of formula IIIb or IIIc and $Y_3$ and $Y_4$ are each an amino radical, or, as the case may be, $R_3$ is a group of formula IVc, can advantageously be prepared in accordance with the following scheme

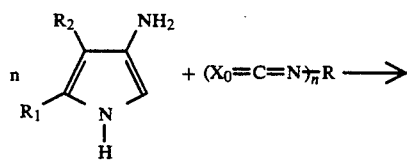

-continued

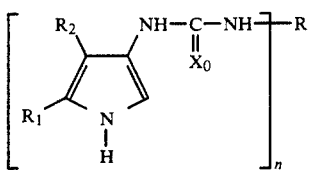

When n is 1 R is, for example, alkyl or phenyl, and when n is 2 R is, for example, alkylene.

The compounds of formula Ib also may be prepared by processes analogous to known processes, for example by reacting glycine nitrile, or a salt thereof, with a corresponding keto compound:

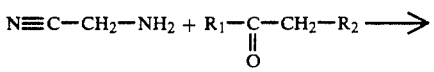

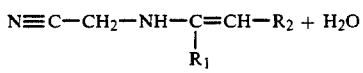

(Ib)

If salts of glycine nitrile are used, it is advantageous to carry out the reaction in the presence of acid-acceptors, for example organic or inorganic bases. The reaction is preferably carried out in lower alcohols or dimethylformamide or dimethylacetamide.

Compounds of formulae I and Ia wherein $X_1$ is hydrogen are advantageously prepared by hydrogenating cleavage of the corresponding compounds of formulae I and Ia wherein $X_1$ is benzyl.

The following Examples further illustrate the invention. Unless stated otherwise, all parts and percentages therein refer to weight.

PREPARATION OF THE INTERMEDIATES

A) Preparation of 2-[1'-methoxycarbonylprop-1'-en-2'-ylamino]acetonitrile

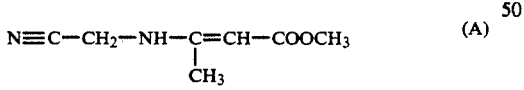

With stirring at 20° C., 167 g (1.65 mol) of triethylamine in 50 ml of absolute methanol are added dropwise to 152.6 g (1.65 mol) of glycine nitrile hydrochloride in 600 ml of absolute methanol in a 2000 ml three-necked flask. The mixture is stirred for 10 minutes and then 174.2 g (1.5 mol) of methyl acetoacetate in 50 ml of absolute methanol are added dropwise. The reaction mixture is heated under reflux for 1 hour. The volatile constituents are removed in vacuo and the residue is taken up in 200 ml of methanol. 1800 ml of ice-water are stirred in, producing a pale yellow precipitate which, after filtration with suction, is treated three times with ice-water. The product is dried until the weight is constant.

Yield: 188.8 g ($\triangleq$81.6% of the theoretical amount)
Melting point: 84° C.

B) Preparation of 2-[1'-benzoylprop-1'-en-2'-ylamino]acetonitrile

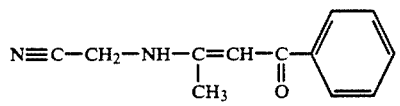

With stirring, 30.8 g (0.2 mol) of glycine nitrile bisulfate and 32.4 g (0.2 mol) of benzoyl acetone are introduced into 400 ml of toluene. 33.6 g (0.4 mol) of sodium bicarbonate are added in portions, $CO_2$ being evolved. After the reaction mixture has been heated under reflux for 1 hour, 1 g of p-toluenesulfonic acid is added. After a reaction time of 4 hours, 10.3 ml of water (calculated: 10.8 ml) have separated under azeotropic conditions. The mixture is filtered. The residue is concentrated and recrystallised from 300 ml of a high-boiling petroleum ether/toluene mixture (1/1) in the presence of activated carbon.

Yield: 27.0 g ($\triangleq$68% of the theoretical amount)
Melting point: 105° C.

C) Preparation of 2-[1'-tert.-butoxycarbonylprop-1'-en-2'-ylamino]acetonitrile

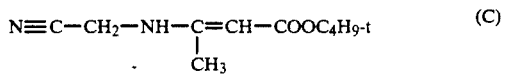

The compound is prepared analogously to A). After removal of the volatile constituents in vacuo, the residue is extracted by shaking with ethyl acetate/water in order to remove the triethylammonium chloride formed. The ester phase is dried and concentrated. The residue is recrystallised from hexane.

Yield: 88% of the theoretical amount
Melting point: 57° C.

D) Preparation of 2-[1'-acetylprop-1'-en-2'-ylamino]acetonitrile

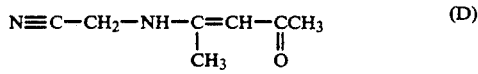

The compound is prepared analogously to A) in dimethylformamide as the reaction medium. The product is recrystallised from isopropyl ether.

Yield: 79% of the theoretical amount
Melting point: 119° C.

E-K) The compounds listed in Table 1 are prepared analogously to A) in dimethylformamide as the reaction medium.

TABLE 1

$$[N\equiv C-CH_2-NH-C(R_1)=CH-]_x-R_2$$

| Compound | x | $R_1$ | $R_2$ | Yield (% of the theoretical amount) melting point |
|---|---|---|---|---|
| E | 1 | $-C_3H_7\text{-n}$ | $-COOCH_3$ | 60.9% - 71° C. |
| F | 1 | $-CH_3$ | $-COO-C_6H_{11}$ (cyclohexyl) | 90% - 79° C.[1] |
| G | 1 | $-CH_3$ | $-COOC_{18}H_{37}\text{-n}$ | 88% - 79° C.[1] |
| H | 1 | $-CH_3$ | $-COOC_2H_4OC_4H_9\text{-n}$ | 78% - 44° C.[2] |
| I | 1 | $-CH_3$ | $-COOC_2H_4SC_2H_5$ | 62% - 77° C.[3] |
| J | 1 | $-CH_3$ | $-CONH-C_6H_5$ | 50% - 110° C. |
| K | 2 | $-CH_3$ | $-COOC_2H_4SC_2H_4OOC-$ | 85% - 157° C.[4] |
| L | 2 | $-CH_3$ | $-COOC_2H_4OOC-$ | 75% - 185° C.[4] |
| M | 1 | $-CH_3$ | $-COOCH_2-C_6H_5$ | 72% - 97° C. |

[1] recrystallised from isopropyl ether
[2] recrystallised from petroleum ether
[3] recrystallised from diethyl ether
[4] recrystallised from dimethylformamide/water

EXAMPLE 1

Preparation of 2-methyl-3-tert.-butoxycarbonyl-4-[2',2'-bis(ethoxycarbonyl)vinyl]aminopyrrole

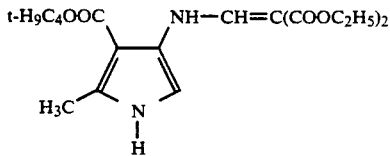

43.2 g (0.24 mol) of a 30% sodium methanolate solution are introduced with stirring into 100 ml of absolute methanol in a 1000 ml three-necked flask. Subsequently, a solution of 39.3 g (0.2 mol) of compound C in 100 ml of absolute methanol is added dropwise and the resulting mixture is heated under reflux for 1 hour. The reaction mixture is then cooled to 20° C. and neutralised with 14.4 g (0.24 mol) of glacial acetic acid. A solution of 43.3 g (0.2 mol) of diethylethoxymethylene malonate is added dropwise and the resulting mixture is again heated under reflux for 1 hour. The virtually clear solution is cooled to 0° C. The resulting precipitate (55.5 g) is filtered off with suction and recrystallised from 800 ml of ethanol in the presence of activated carbon.

Yield: 49.2 g ($\triangleq$67.1% of the theoretical amount)
Melting point: 189° C.

EXAMPLES 2-6

The compounds listed in Table 2 are prepared analogously to Example 1.

TABLE 2

Pyrrole structure with $H_3C$ at 2-position, $R_2$ at 3-position, and $NH-CH=C(Y_1)(Y_2)$ at 4-position, NH at 1-position.

| Ex. | intermediate used | $R_2$ | $Y_1$ | $Y_2$ | Yield (% of the theoretical amount) melting point |
|---|---|---|---|---|---|
| 2 | A | $-COOCH_3$ | $-COOC_2H_5$ | $-CN$ | 84% - 183° C. |

TABLE 2-continued

Structure:

R₂ at 3-position, NH—CH=C(Y₁)(Y₂) at 4-position of pyrrole with H₃C at 2-position, NH.

| Ex. | intermediate used | R₂ | Y₁ | Y₂ | Yield (% of the theoretical amount) melting point |
|---|---|---|---|---|---|
| 3 | B | —C(=O)—C₆H₅ | —COOC₂H₅ | —COOC₂H₅ | 54% - 215° C.[5] |
| 4 | A | —COOCH₃ | —COOC₂H₅ | —CCH₃(=O) | 66% - 180° C.[6] |
| 5 | A | —COOCH₃ | —CCH₃(=O) | —CCH₃(=O) | 60% - 192° C.[6] |
| 6 | A | —COOCH₃ | —COOC₂H₅ | —C(=O)—C₆H₅ | 64% - 171° C.[6] |

[5] recrystallised from ethanol/activated carbon
[6] recrystallised from methanol/activated carbon

EXAMPLE 7

Preparation of 2-methyl-3-methoxycarbonyl-4-benzoylaminopyrrole

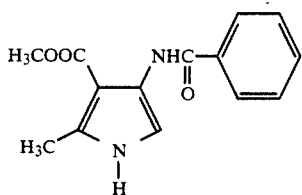

15.4 g (0.1 mol) of compound A are introduced with stirring into 80 ml of absolute methanol in a 500 ml three-necked flask. 21.6 g (0.1 mol) of a 30% sodium methanolate solution are added dropwise and the reaction mixture is heated under reflux for 1 hour. The reaction mixture is then neutralised with 7.2 g (0.12 mol) of glacial acetic acid. 12.1 g (0.12 mol) of triethylamine and 14.1 g (0.1 mol) of benzoyl chloride are added dropwise.

The reaction mixture is stirred at room temperature for a further 30 minutes. After cooling to 0° C., 1 liter of ice-water is added. The resulting precipitate is filtered off with suction, washed free of chloride and dried until the weight is constant. The produce is recrystallised from methanol/activated carbon.

Yield: 19 g (≙74% of the theoretical amount)
Melting point: 183° C.

EXAMPLES 8-20

The compounds listed in Table 3 are prepared analogously to Example 7.

TABLE 3

Structure: R₂ at 3-position, NH—R₃ at 4-position of pyrrole with H₃C at 2-position, NH.

| Ex. | intermediate used | R₂ | R₃ | Yield (% of the theoretical amount) melting point |
|---|---|---|---|---|
| 8 | A | —COOCH₃ | 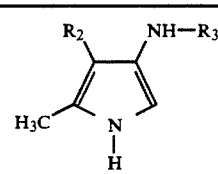 —C(=O)—C₆H₄—C₄H₉-t | 66% - 220° C.[6] |

TABLE 3-continued

Structure:
R2 at 4-position, NH—R3 at 3-position, H3C at 5-position of pyrrole (N—H)

| Ex. | intermediate used | R$_2$ | R$_3$ | Yield (% of the theoretical amount) melting point |
|---|---|---|---|---|
| 9 | A | —COOCH$_3$ | —C(=O)—(2,4-dichlorophenyl) | 70.2% - 234° C. |
| 10 | A | —COOCH$_3$ | —C(=O)—CH=CH—phenyl | 48.9% - 209° C.[6] |
| 11 | A | —COOCH$_3$ | —C(=O)CH$_3$ | 143° C.[7] |
| 12 | A | —COOCH$_3$ | —C(=O)C$_4$H$_9$-t | 71% - 164° C.[7] |
| 13 | A | —COOCH$_3$ | —C(=O)C$_{15}$H$_{31}$-n | 70% - 78° C.[6] |
| 14 | A | —COOCH$_3$ | —COOC$_2$H$_5$ | 80% - 136° C.[8] |
| 15 | A | —COOCH$_3$ | —COOC$_4$H$_9$-n | 85.7% - 91° C. |
| 16 | A | —COOCH$_3$ | —COOC$_{16}$H$_{33}$-n | 70% - 94° C.[6] |
| 17 | A | —COOCH$_3$ | —SO$_2$—phenyl | 79% - 223° C.[8] |
| 18 | A | —COOCH$_3$ | triazine with two OCH$_2$CH=CH$_2$ groups | 69% - 170° C.[8] |
| 19 | H | —COOC$_2$H$_4$OC$_4$H$_9$-n | —C(=O)—phenyl | 94° C.[9] |
| 20 | I | —COOC$_2$H$_4$SC$_2$H$_5$ | —C(=O)—phenyl | 129° C.[10] |

[6] recrystallised from methanol/activated carbon
[7] recrystallised from isopropyl ether/activated carbon
[8] recrystallised from methanol/water
[9] reaction in ethylene glycol monobutyl ether instead of methanol
[10] reaction in 3-thiapentanol instead of methanol

EXAMPLE 21

Preparation of 2-methyl-3-methoxycarbonyl-4-phenylaminooxalyl-aminopyrrole

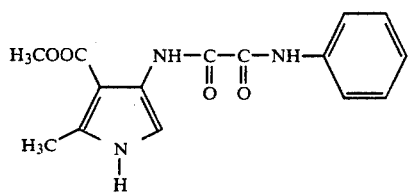

In a 250 ml three-necked flask, a solution consisting of 12.0 g (0.078 mol) of compound A and 16.2 g (0.09 mol) of 30% sodium methanolate in 60 ml of absolute methanol is heated under reflux for 30 minutes. The reaction mixture is then neutralised with 5.4 g (0.09 mol) of glacial acetic acid. 9.1 g (0.09 mol) of triethylamine and then 10.6 g (0.078 mol) of oxalic ester chloride are added dropwise. The reaction mixture is stirred for a further hour at room temperature. After the volatile constituents have been removed in vacuo, 37.2 g (0.4 mol) of aniline are added to the reaction mixture which is then heated at 160° C. with stirring, the ethanol distilling off. The excess aniline is removed in vacuo and the reaction mixture is extracted twice with methylene chloride/water. The dark residue obtained from the methylene chloride phase is dissolved in 75 ml of dimethylformamide, treated with activated carbon and stirred into 250 ml of water. The resulting precipitate is filtered, washed and dried until the weight is constant.

Yield: 10.2 g ($\hat{=}$42.3% of the theoretical amount)
Melting point: 250° C. (decomposition)

EXAMPLE 22

Preparation of 2-methyl-3-cyclohexyloxycarbonyl-4-benzoylaminopyrrole

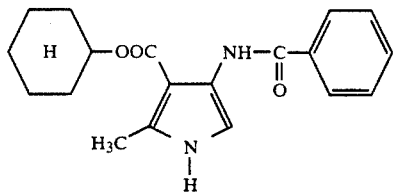

In a 100 ml three-necked flask, 15.5 g (0.06 mol) of compound 7 together with 50 ml of cyclohexanol are heated at 160° C., with stirring, in the presence of 0.5 g of titanium butanolate (catalyst). After a reaction time of 5 hours, catalyst is again added. After about 15 hours, the quantitative amount of methanol (2.4 ml) has separated. The dark reaction solution is freed of volatile constituents in vacuo, and the residue is taken up in methylene chloride and extracted twice by shaking with water. When the organic phase has been dried it is taken up in 100 ml of isopropanol with the addition of activated carbon and, while stirring, 250 ml of water are added. The resulting precipitate is recrystallised from methanol.

Yield: 16.3 g ($\hat{=}$83% of the theoretical amount)
Melting point: 176° C.

2-Methyl-3-cyclohexyloxycarbonyl-4-benzoylaminopyrrole can also be prepared analogously to Example 24 using compound F.

EXAMPLE 23

Preparation of 2-methyl-3-n-octadecyloxycarbonyl-4-benzoylaminopyrrole

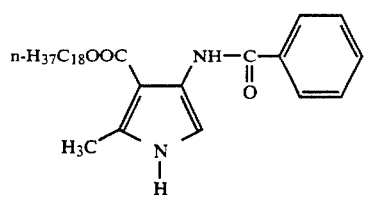

The compound is prepared analogously to Example 22.

Melting point: 96° C.

2-Methyl-3-n-octadecyloxycarbonyl-4-benzoylaminopyrrole can also be prepared analogously to Example 24 using compound G.

EXAMPLE 24

Preparation of 2-methyl-3-(5'-hydroxy-3'-thiapentyl)-4-benzoylaminopyrrole

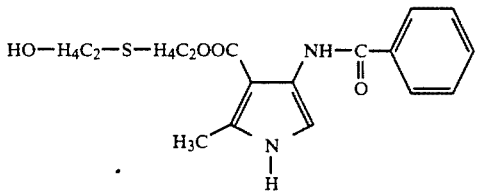

21.6 g (0.12 mol) of 30% sodium methanolate solution are placed in a 250 ml three-necked flask. The methanol is removed, as far as possible quantitatively, in vacuo. 70 ml of thiodiglycol are added and the mixture is heated to 60° C. The remaining methanol is removed in vacuo. 18.3 g of compound K are then added. The reaction mixture is heated at 80° C. for 30 minutes. Then, 30 ml of thiodiglycol are added and the reaction mixture is cooled to room temperature. 7.2 g (0.12 mol) of glacial acetic acid are added dropwise. After the addition of 12.1 g (0.12 mol) of triethylamine and 14.1 g (0.1 mol) of benzoyl chloride, the mixture is stirred at room temperature for a further 30 minutes. Subsequently, the reaction mixture is extracted by shaking with ethyl acetate/water, and the organic phase is separated and treated with activated carbon. The volatile constituents are removed in vacuo. The residue is chromatographed over silica gel using methylene chloride/acetone (3/7) and the eluate is concentrated in vacuo. The residue is then dissolved in 400 ml of methylene chloride/acetone (4/2) and precipitated with 600 ml of petroleum ether with stirring. The resulting precipitate is dried until the weight is constant.

Yield: 15.0 g ($\hat{=}$43% of the theoretical amount)
Melting point: 114° C.

EXAMPLE 25

Preparation of
2-methyl-3-anilinocarbonyl-4-benzoylaminopyrrole

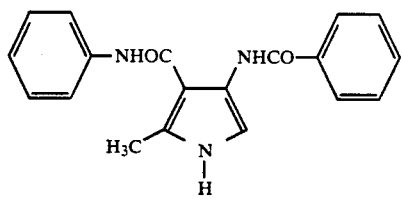

In a 250 ml three-necked flask, 20.5 g (0.095 mol) of compound J are dissolved with stirring in 100 ml of methanol. 18.9 g (0.105 mol) of a 30% sodium methanolate solution are added dropwise and the reaction mixture is heated under reflux for 30 minutes. After cooling to room temperature, 6.3 g (0.105 mol) of glacial acetic acid are added. The reaction mixture is stirred for 10 minutes and then 10.6 g (0.105 mol) of triethylamine are added dropwise. After the addition of 13.4 g (0.095 mol) of benzoyl chloride, the reaction mixture is stirred at room temperature for a further hour. It is then poured into ice-water, and the precipitate formed is washed free of salt. The resulting product is dried until the weight is constant.

Yield: 28.7 g ($\triangleq$94.7% of the theoretical amount)
Melting point: 267° C.

EXAMPLE 26

Preparation of
2-methyl-3-tert.-butoxycarbonyl-4-benzoylaminopyrrole

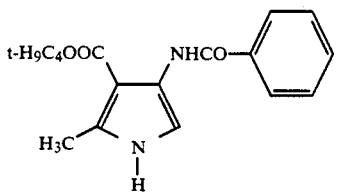

In a 250 ml three-necked flask, 16.3 g (0.083 mol) of compound C are introduced into 100 ml of methanol. With stirring, 18.0 g (0.1 mol) of a 30% sodium methanolate solution are added dropwise and the reaction mixture is heated under reflux for 30 minutes. It is then neutralised with 6.0 g (0.1 mol) of glacial acetic acid, and 10.1 g (0.1 mol) of triethylamine are added. After the dropwise addition of 11.7 g (0.083 mol) of benzoyl chloride, the reaction mixture is left to stand overnight. The precipitate formed is filtered off. The filtrate is concentrated and the resulting residue is estracted in portions with isopropyl ether. The extracts are concentrated and cooled to give a beige-coloured precipitate which is dried until the weight is constant.

Yield: 11.3 g ($\triangleq$45.4 % of the theoretical amount)
Melting point: 170° C.

EXAMPLE 27

Preparation of
2-n-propyl-3-methoxycarbonyl-4-benzoylaminopyrrole

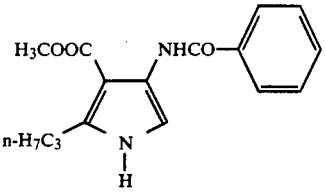

In a 250 ml three-necked flask, 27.3 g (0.15 mol) of compound E are dissolved in 80 ml of methanol and, with stirring, 30.6 g (0.17 mol) of a 30% sodium methanolate solution are added dropwise. After heating under reflux for 30 minutes, the reaction mixture is cooled to room temperature. First, 10.2 g (0.17 mol) of glacial acetic are added, then, after 10 minutes, 17.2 g (0.17 mol) of triethylamine followed by 21.1 g (0.15 mol) of benzoyl chloride are added dropwise. The reaction mixture is left to stand overnight. It is stirred into ice-water and the resulting precipitate is filtered off, washed free of salt and dried until the weight is constant.

Yield: 38.6 g ($\triangleq$95 % of the theoretical amount)
Melting point: 128° C.

EXAMPLE 28

Preparation of
2-methyl-3-benzyloxycarbonyl-4-benzoylaminopyrrole

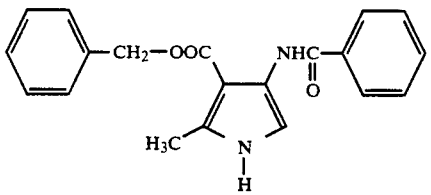

In a 250 ml three-necked flask fitted with a separator, 38.7 g (0.15 mol) of the compound obtained in Example 7 are heated at 190° C. for 5 hours, with stirring, with 100 ml of benzyl alcohol in the presence of titanium butanolate. At the beginning of the reaction, first of all 1 ml of titanium butanolate is added and then, after 3 hours, a further 1 ml. In the course of the reaction 2.3 ml (calculated: 2.4 ml) of methanol pass over. The resulting dark solution is concentrated to a residue in vacuo. The unreacted benzyl alcohol is recovered. The distillation residue is dissolved in 400 ml of acetone, 15 ml of water are added, and the batch is treated with activated carbon and stirred into 1.5 liters of ice-water. The resulting precipitate is filtered off with suction and dried until the weight is constant.

Yield: 46.1 g ($\triangleq$91.8 % of the theoretical amount)
Melting point: 137° C.

2-Methyl-3-benzyloxycarbonyl-4-benzoylaminopyrrole can also be prepared analogously to Example 24 using compound M.

EXAMPLE 29

Preparation of
2-methyl-3-tert.-butoxycarbonyl-4-acetylaminopyrrole

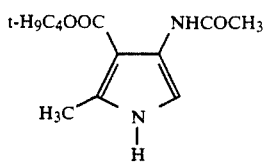

19.6 g (0.10 mol) of compound C are dissolved in 100 ml of methanol in a 250 ml three-necked flask. After the addition of 21.6 g (0.12 mol) of a 30% sodium methanolate solution, the reaction mixture is heated under reflux for 1 hour. After cooling to room temperature, 14.4 g (0.24 mol) of glacial acetic acid are added to the reaction mixture which is then left to stand overnight. It is stirred into ice-water and the resulting precipitate is washed free of salt and dried until the weight is constant.

Yield: 15.4 g ($\triangleq$68.9% of the theoretical amount)
Melting point: 214° C.

EXAMPLE 30

Preparation of a mixture of
2-methyl-3-tert.-butoxycarbonyl-4-methoxyoxalylaminopyrrole and
2-methyl-3-tert.-butoxycarbonyl-4-ethoxyoxalylaminopyrrole in a molar ratio of 4:1

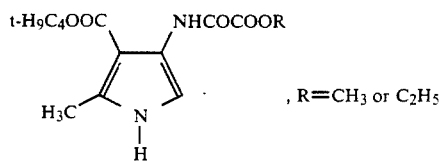

19.8 g (0.11 mol) of a 30% sodium methanolate solution are added dropwise, with stirring, to 19.6 g (0.10 mol) of compound C in a 250 ml three-necked flask. The reaction mixture is heated under reflux for 30 minutes. After cooling to room temperature, 6.6 g (0.11 mol) of glacial acetic acid followed by 11.1 g (0.11 mol) of triethylamine and 13.7 g (0.10 mol) of oxalic acid ethyl ester chloride are added. The reaction mixture is left to stand overnight. It is stirred into ice-water. The resulting precipitate is filtered off, washed free of salt and dried until the weight is constant.

Yield: 22.6 g
Melting point: 171° C.

The resulting mixture may, if desired, be separated by chromatographic methods.

EXAMPLE 31

Preparation of
2-methyl-3-methoxycarbonyl-4-diethylaminocarbonylaminopyrrole

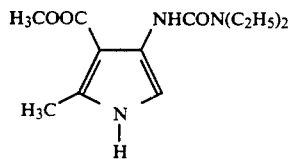

23.1 g (0.15 mol) of compound A are dissolved in 80 ml of methanol in a 250 ml three-necked flask. 29.7 g (0.165 mol) of a 30% sodium methanolate solution are added dropwise with stirring. The reaction mixture is heated under reflux for 30 minutes. After cooling to room temperature, the reaction mixture is neutralised with 9.9 g (0.165 mol) of glacial acetic acid. There are then added 16.7 g (0.165 mol) of triethylamine and 20.3 g (0.15 mol) of N,N-diethylcarbamic acid chloride. The reaction mixture is left to stand overnight and is concentrated. The residue is treated with methylene choride/water and filtered off. The two phases are separated. After removal of the solvent, 23.3 g of a residue remain from the organic phase, which is extracted with isopropyl ether. The extract is treated with activated carbon, concentrated and stirred into low-boiling petroleum ether. The precipitate formed is filtered and dried.

Melting point: 125° C.

EXAMPLE 32

Preparation of
2-methyl-3-methoxycarbonyl-4-dimethylaminothiocarbonylaminopyrrole

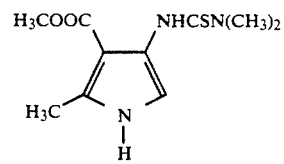

23.1 g (0.15 mol) of compound A are introduced into 80 ml of methanol in a 250 ml three-necked flask. After the addition of 29.7 g (0.165 mol) of a 30% sodium methanolate solution, the reaction mixture is heated under reflux for 30 minutes. It is cooled to room temperature and neutralised with 9.9 g (0.165 mol) of glacial acetic acid. There are then added 16.7 g (0.165 mol) of triethylamine and 18.5 g (0.15 mol) of N,N-dimethylthiocarbamic acid chloride. The reaction mixture is left to stand overnight and is stirred into ice-water. The precipitate is filtered, washed free of salt and extracted with methanol. The residue which remains is again filtered, washed and dried.

Yield: 15.2 g ($\triangleq$42% of the theoretical amount)
Melting point: 226° C.

EXAMPLE 33

Preparation of
2-methyl-3-(4'-hydroxybutoxycarbonyl)-4-benzoylaminopyrrole

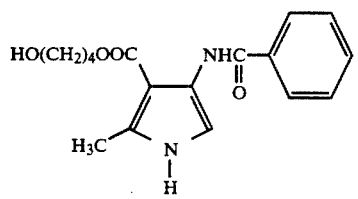

The compound is prepared analogously to Example 28 using excess butanediol. The reaction is carried out at 180° C. for 5 hours.

Yield: 70% of the theoretical amount
Melting point: 110° C.

2-Methyl-3-(4'-hydroxybutoxycarbonyl)-4-benzoylaminopyrrole can also be prepared analogously to Example 24 using compound L.

EXAMPLE 34

Preparation of
2-methyl-3-methoxycarbonyl-[4-2',2'-bis(ethoxycarbonyl)vinyl]aminopyrrole

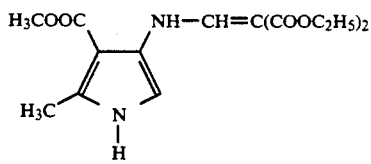

The product is prepared analogously to Example 1 using compound A.

Yield: 71% of the theoretical amount
Melting point: 190°-192° C. (after recrystallisation from ethanol/petroleum ether).

EXAMPLE 35

Preparation of
2-methyl-3-carboxy-4-benzoylaminopyrrole

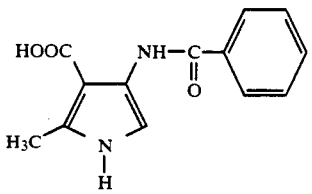

25.8 g (0.01 mol) of the compound obtained in Example 28 are dissolved at room temperature, with stirring, in 150 ml of dimethylacetamide. After the addition of 5 g of palladium-containing carbon (5% Pd on activated carbon), hydrogenation is carried out at an excess pressure of 4 bar. After 70 minutes, the absorption of hydrogen is complete. The catalyst is filtered off and the reaction mixture is concentrated to a residue in vacuo. The residue is then dissolved in 300 ml of methanol. After treatment with activated carbon, the solution is stirred into ice-water. The resulting precipitate is filtered off and dried until the weight is constant.

Yield: 11.1 g ($\hat{=}$55.5% of the theoretical amount)
Melting point: 237° C.

EXAMPLE 36

Preparation of
2-methyl-3-methoxycarbonyl-4-(n-octylthio)carbonylaminopyrrole

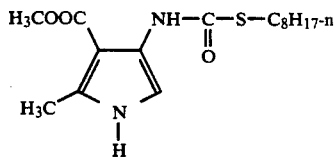

The compound is prepared analogously to Example 7. 25.1 g (0.12 mol) of n-octylthiochloroformate are used as the acylating reagent. When the reaction has ended, the reaction mixture is concentrated to a residue which is then dissolved in ethyl acetate/water. The resulting two-phase system is extracted twice by shaking with water. The organic phase is dried and concentrated to a residue which is subsequently recrystallised from 100 ml of methanol. The product is in the form of the hemihydrate.

Yield: 23.6 g ($\hat{=}$58.6% of the theoretical amount)
Melting point: 81° C.

EXAMPLE 37

Preparation of
2-methyl-3-methoxycarbonyl-4-anilinothiocarbonylaminopyrrole

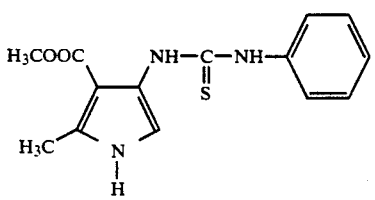

The preparation is carried out analogously to Example 7. 25.4g (0.19 mol) of phenyl isothiocyanate are used as the acylating reagent. When the reaction has ended, ice-water is added to the reaction mixture. The precipitate formed is dried and recrystallised from acetone/activated carbon. The product is in the form of the hydrate ($\frac{1}{3}$ mol $H_2O$ per mol pyrrole).

Yield: 57.2% of the theoretical amount
Melting point: 200° C.

EXAMPLE 38

Preparation of
2-methyl-3-methoxycarbonyl-4-n-octylaminothiocarbonylaminopyrrole

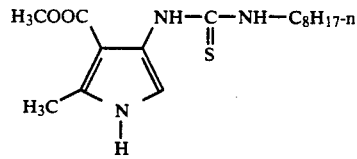

Preparation and working up are carried out analogously to Example 37. 20.5 g (0.12mol) of octyl isothiocyanate are used as the acylating reagent. After recrystallisation from methanol/activated carbon, the product is in the form of the monohydrate.

Yield: 41.8%
Melting point: 103° C.

EXAMPLES 39–44

The compounds listed in Table 4 are prepared analogously to Example 21.

TABLE 4

[H3COOC, NH—R3 structure with H3C, N-H pyrrole, bracketed ]2

| Ex. | intermediate used | R3 | Yield (% of the theoretical amount) melting point |
|---|---|---|---|
| 39 | A | —C(O)—(CH2)4—C(O)— | 53% - 270° C. |
| 40 | A | —C(O)—(CH2)8—C(O)— | 71% - 205° C.[11] |
| 41 | A | —CO—(CH2)6—OC— | 49% - 191° C.[11] |
| 42 | A | —C(O)—(p-C6H4)—C(O)— | 68% - >200° C. (decomposition) |
| 43 | A | —C(O)—(m-C6H4)—C(O)— | 56% - >200° C.[11] (decomposition) |
| 44 | A | triazine with OC3H7-i | 48% - 190° C.[8] |

[8] recrystallised from methanol/water
[11] recrystallised from dimethylformamide/water

EXAMPLE 45

Preparation of 1,5-bis[(2'-methyl-3'-methoxycarbonylpyrrol-4'-yl)carbamoyloxy]-3-oxapentane

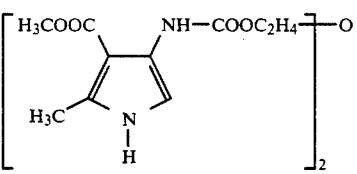

A solution of 18.5 g (0.12 mol) of compound A in 100 ml of absolute methanol is heated under reflux together with 25.9 g (0.144 mol) of sodium methanolate (30% in methanol) for 30 minutes. After cooling to room temperature, the mixture is neutralised with 8.64 g (0.144 mol) of glacial acetic acid. There are then added, in succession, 14.6 g (0.144 mol) of triethylamine and 13.9 g (0.06 mol) of diglycol bis[chloroformate], the temperature being maintained at 10° C. by cooling. When the reaction is complete, the batch is cooled to 0° C. The resulting precipitate is filtered off with suction, washed in succession with cold methanol and water and dried until the weight is constant. For further purification, the product is recrystallised from acetone/dimethylacetamide (6:1) in the presence of activated carbon. The product is in the form of the monohydrate.

Yield: 26% of the theoretical amount
Melting point: 206° C.

EXAMPLE 46

Preparation of 1,6-bis[(2'-methyl-3'-methoxycarbonylpyrrol-4'-yl)carbamoylamino]hexane

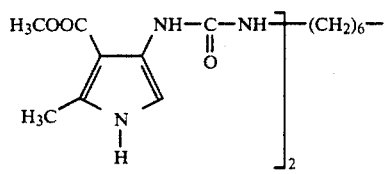

Preparation and working up are carried out analogously to Example 45. 10.1 g (0.06 mol) of hexamethylene diisocyanate are used as the acylating reagent. The product is in the form of the tetrahydrate.

Yield: 30.7% of the theoretical amount
Melting point: 136° C.

EXAMPLE 47

The dry mixture given below is rolled in a roll mill for 5 minutes at 180° C. Foil specimens of the 0.3 mm thick rolled sheet formed are thermally stressed at 180° C. in a drying cabinet. The Yellowness Index (YI) of the samples is determined according to ASTM D 1925 at regular intervals. The results are set forth in Tables 5 and 6a–6c.

TABLE 5

Dry mixture:
100 parts S-PVC (®Solvic 268 GA),
2 parts epoxidised soybean oil,
0.5 part of the compound indicated.

| Compound from Ex. | YI values after stress time in minutes | | | | |
|---|---|---|---|---|---|
| | 0 | 5 | 10 | 15 | 20 |
| — | 39.5 | 32.0 | 34.0 | 39.2 | 62.2 |
| 7 | 8.9 | 7.6 | 8.0 | 8.6 | 10.2 |
| 12 | 5.8 | 5.0 | 5.6 | 7.3 | 8.4 |
| 14 | 6.3 | 5.4 | 5.9 | 8.1 | 10.5 |

TABLES 6a–6c 100 parts S-PVC (®Solvic 268 GA),
3 parts epoxidised soybean oil,
0.35 part calcium stearate,
0.15 part zinc stearate,
0.55 part diisodecyl phenyl phosphite,
0.3 part of the compound indicated.

a)

| Compound from Ex. | YI values after stress time in minutes | | | | | | |
|---|---|---|---|---|---|---|---|
| | 0 | 5 | 10 | 15 | 20 | 25 | 30 |
| — | 16.9 | 20.2 | 24.7 | 34.5 | 38.4 | 36.0 | 35.4 |
| 7 | 4.4 | 6.2 | 8.3 | 11.4 | 14.1 | 18.9 | 25.0 |
| 8 | 4.2 | 6.9 | 9.3 | 12.5 | 14.5 | 17.1 | 22.9 |
| 12 | 3.6 | 5.5 | 7.9 | 12.4 | 14.6 | 18.4 | 24.1 |
| 14 | 4.4 | 6.3 | 9.0 | 12.9 | 15.8 | 18.4 | 24.2 | b)

| Compound from Ex. | YI values after stress time in minutes | | | | | | |
|---|---|---|---|---|---|---|---|
| | 0 | 5 | 10 | 15 | 20 | 25 | 30 |
| — | 21.9 | 25.6 | 32.3 | 39.6 | 40.7 | 39.1 | 43.4 |
| 13 | 8.8 | 9.6 | 12.7 | 16.2 | 20.2 | 22.5 | 26.8 |
| 16 | 9.9 | 10.9 | 13.7 | 18.1 | 20.8 | 23.1 | 27.9 | c)

TABLES 6a-6c-continued

| Compound from Ex. | YI values after stress time in minutes | | | | | |
|---|---|---|---|---|---|---|
| | 0 | 5 | 10 | 15 | 20 | 25 |
| — | 19.4 | 20.3 | 28.7 | 39.0 | 39.0 | 36.1 |
| 18 | 7.8 | 8.4 | 11.6 | 15.2 | 19.6 | 24.1 |
| 19 | 8.6 | 9.5 | 11.8 | 16.2 | 20.4 | 22.9 |
| 22 | 5.8 | 6.1 | 10.4 | 14.9 | 18.3 | 20.6 |
| 24 | 7.1 | 7.6 | 9.2 | 14.4 | 18.2 | 21.7 |

EXAMPLE 48

The dry mixture given below is rolled in a roll mill for 5 minutes at 190° C. A foil strip of the 0.3 mm thick rolled sheet formed is tested at 180° C. in a ®Mathis-Thermotester. The Yellowness Index (YI) of the samples is determined according to ASTM D 1925 at regular intervals. The results are set forth in Table 7.

TABLE 7

Dry mixture:

100 parts S-PVC (®Vestolit S 6058),
5 parts epoxidised soybean oil,
0.2 part montanic acid ester wax,
0.8 part diisodecyl phenyl phosphite,
0.6 part of the compound indicated.

| Compound from Ex. | YI values after stress time in minutes | | | | | | |
|---|---|---|---|---|---|---|---|
| | 0 | 5 | 10 | 15 | 20 | 25 | 30 |
| 18 | 9.2 | 11.5 | 12.9 | 16.1 | 22.9 | 29.5 | 34.9 |
| 37 | 5.7 | 10.4 | 12.0 | 15.7 | 19.9 | 25.3 | 30.6 |
| — | In the processing of the dry mixture indicated, a dark sheet which adheres to the roller is obtained. | | | | | | |

EXAMPLE 49

The dry mixture given below is rolled in a roll mill for 5 minutes at 190° C. Foil specimens of the 0.3 mm thick rolled sheet formed are thermally stressed at 180° C. in a drying cabinet. The Yellowness Index (YI) of the samples is determined according to ASTM D 1925 at regular intervals. The results are set forth in Table 8.

TABLE 8

Dry mixture:

100 parts PVC (®Vinnol H 70 DF),
17 parts dioctyl phthalate,
3 parts epoxidised soybean oil,
0.33 part zinc oleate,
0.53 part barium p-(tert.-butyl) benzoate,
0.7 part diisodecyl phenyl phosphite,
0.44 part ®SHELL SOL A (aromatic hydrocarbon mixture),
0.2 part of the compound indicated.

| Compound from Ex. | YI values after stress time in minutes | | | | | | |
|---|---|---|---|---|---|---|---|
| | 0 | 5 | 10 | 15 | 20 | 25 | 30 |
| — | 10.5 | 11.9 | 14.6 | 19.6 | 26.1 | 30.1 | 31.5 |
| 22 | 4.7 | 7.0 | 8.4 | 9.0 | 10.8 | 13.1 | 15.5 |
| 24 | 5.4 | 6.5 | 8.1 | 10.3 | 13.1 | 15.6 | 19.2 |

What is claimed is:

1. A composition containing a) a chlorine-containing polymer and b) an effective thermal or light stabilizing amount of a compound of formula I

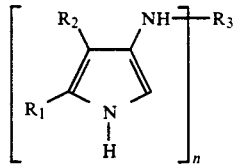

wherein n is 1 or 2, $R_1$ is $C_1$-$C_4$alkyl, $R_2$ is a group of formula IIa, IIb, IIc or IId

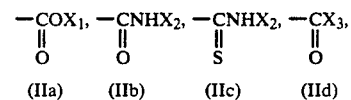

$X_1$ is hydrogen, $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, hydroxy, methoxy or/and by ethoxy, $C_7$-$C_{10}$phenylalkyl or $C_7$-$C_{10}$phenylalkyl substituted in the phenyl radical by $C_1$-$C_{20}$alkyl, chlorine, hydroxy, methoxy or/and by ethoxy, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is a group of formula IIIa to IIIg

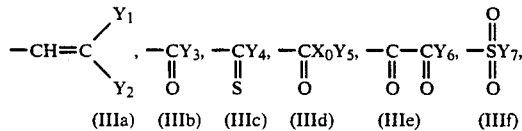

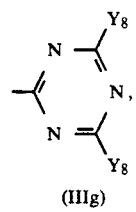

$X_0$ is an oxygen atom or a sulfur atom, $Y_1$ and $Y_2$ are each independently of the other —CN, benzoyl, $C_2$-$C_4$alkanoyl or $C_2$-$C_4$alkoxycarbonyl, $Y_3$ is $C_1$-$C_{20}$alkyl, $C_3$-$C_{20}$alkenyl, phenyl, phenyl substituted by $C_1$-$C_4$alkyl, chlorine, —$NO_2$, methoxy or/and by ethoxy, 2-phenylethenyl, di($C_1$-$C_4$alkyl)amino, diphenylamino, $C_1$-$C_{20}$alkylamino, $C_3$-$C_8$cycloalkylamino, phenylamino, phenylamino substituted in the phenyl ring by $C_1$-$C_4$alkyl, chlorine, hydroxy, methoxy or/and by ethoxy, benzylamino, benzenesulfonamido or toluenesulfonamido, $Y_4$ is di($C_1$-$C_4$alkyl)amino, diphenylamino, $C_1$-$C_8$alkylamino, phenylamino, phenylamino substituted in the phenyl ring by $C_1$-$C_4$alkyl, chlorine, hydroxy, methoxy or/and by ethoxy, or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, $C_7$-$C_{10}$phenylalkyl or $C_7$-$C_{10}$phenylalkyl substituted in the phenyl radical by $C_1$-$C_{20}$alkyl, $Y_6$ is $C_1$-$C_4$alkoxy, phenylamino or phenylamino substituted in the phenyl group by $C_1$-$C_4$alkyl, chlorine, hydroxy, methoxy or/and by ethoxy, $Y_7$ is $C_1$-$C_4$alkyl, phenyl or phenyl substituted by $C_1$-$C_4$alkyl, chlorine, —$NO_2$, ($C_1$-$C_{12}$alkyl) oxycarbonyl and/or by phenoxycarbonyl, the radicals $Y_8$ are each independently of the other $C_1$-$C_4$alkoxy or allyloxy, and when n is 2 $R_3$ is a group of formula IVa, IVb, IVc or IVd

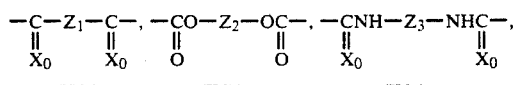

(IVa)  (IVb)  (IVc)

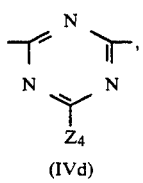

(IVd)

$X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

2. A composition according to claim 1, wherein n is 1 or 2, $R_1$ is $C_1$-$C_4$alkyl, $R_2$ is a group of formula IIa, IIb, IIc or IId, $X_1$ is $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_1$-$C_{20}$alkyl, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is group of formula IIIa to IIIg, $X_0$ is an oxygen atom, $Y_1$ and $Y_2$ are each independently of the other —CN, benzoyl, $C_2$-$C_4$alkanoyl or $C_2$-$C_4$alkoxycarbonyl, $Y_3$ is $C_1$-$C_{20}$alkyl, $C_3$-$C_{20}$alkenyl, phenyl, phenyl substituted by $C_1$-$C_4$alkyl, chlorine, methoxy or/and by ethoxy, 2-phenylethenyl, di($C_1$-$C_4$alkyl)amino, $C_1$-$C_8$alkylamino, phenylamino, benzylamino, benzenesulfonamido or toluenesulfonamido, $Y_4$ is di($C_1$-$C_4$alkyl)amino, $C_1$-$C_8$alkylamino, phenylamino or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, $C_7$-$C_{10}$phenylalkyl or $C_7$-$C_{10}$phenylalkyl substituted in the phenyl radical by $C_1$-$C_{20}$alkyl, $Y_6$ is $C_1$-$C_4$alkoxy, phenylamino or phenylamino substituted in the phenyl group by $C_1$-$C_4$alkyl, chlorine, methoxy or/and by ethoxy, $Y_7$ is phenyl or tolyl, the radicals $Y_8$ are each independently of the other $C_1$-$C_4$alkoxy or allyloxy, and when n is 2 $R_3$ is a group of formula IVa, IVb, IVc or IVd, $X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

3. A composition according to claim 1, wherein $X_1$ is $C_1$-$C_{18}$alkyl, $C_3$-$C_6$alkyl interrupted by one or two oxygen atoms or sulfur atoms or/and substituted by OH, allyl, methallyl, oleyl, $C_5$-$C_8$cycloalkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_8$-$C_{14}$alkyl, $X_3$ is methyl, ethyl or phenyl, $Y_3$ is $C_1$-$C_{18}$alkyl, allyl, methallyl, oleyl, phenyl, phenyl substituted by $C_1$-$C_4$alkyl, chlorine, methoxy or/and by ethoxy, 2-phenylethenyl or di($C_1$-$C_4$alkyl)amino, and $Y_5$ is $C_1$-$C_{18}$alkyl, $C_5$-$C_8$cycloalkyl, phenyl, $C_7$-$C_{10}$phenylalkyl or $C_7$-$C_{10}$phenylalkyl substituted in the phenyl radical by $C_8$-$C_{14}$alkyl.

4. A composition according to claim 1, wherein $R_1$ is methyl.

5. A composition according to claim 1, wherein n is 1, $R_2$ is a group of formula IIa or IIc, and $R_3$ is a group of formula IIIb, IIId or IIIg.

6. A composition according to claim 1, wherein n is 1, $R_1$ is methyl, $R_2$ is a group of formula IIa, $X_1$ is $C_1$-$C_{12}$alkyl, $R_3$ is a group of formula IIIb, IIId or IIIg, $Y_3$ is $C_1$-$C_{18}$alkyl, allyl, phenyl or phenyl substituted by $C_1$-$C_4$alkyl, chlorine, methoxy or/and by ethoxy, and $Y_5$ is $C_1$-$C_{18}$alkyl, cyclohexyl, phenyl or benzyl.

7. A composition according to claim 1, wherein n is 2.

8. A composition according to claim 1, wherein n is 2 and $R_3$ is a group of formula IVa or IVb.

9. A composition according to claim 1, wherein $R_2$ is a group of formula IIa.

10. A composition according to claim 1, wherein the compound of formula I is 2-methyl-3-methoxycarbonyl-4-ethoxycarbonylaminopyrrole, 2-methyl-3-methoxycarbonyl-4-benzoylaminopyrrole, 2-methyl-3-methoxycarbonyl-4-(2',4'-diallyloxy-1',3',5'-triazin-6'-yl)aminopyrrole, 1,4-bis[(2'-methyl-3'-methoxycarbonylpyrrol-4'-yl)carbamoyl]butane or 1,6-bis[(2'-methyl-3'-methoxycarbonylpyrrol-4'-yl)carbamoyloxy]hexane.

11. A composition according to claim 1, wherein the chlorine-containing polymer is polyvinyl chloride.

12. A composition according to claim 1 containing, in addition, an effective stabilising amount of a Me(II) carboxylate and/or Me(II) phenolate wherein Me(II) is Ba, Ca, Mg, Cd or Zn.

13. A composition according to claim 1 containing, in addition, an epoxy compound and/or a phosphite.

14. A method for stabilising a chlorine-containing polymer against thermal and light-induced degradation, which method comprises incorporating in said polymer an effective stabilising amount of a compound of formula I.

15. Compounds of formula Ia

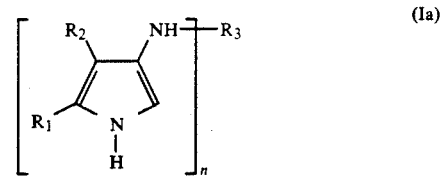

wherein n is 1 or 2, $R_1$ is $C_1$-$C_4$alkyl, $R_2$ is a group of formula IIa, IIb, IIc or IId

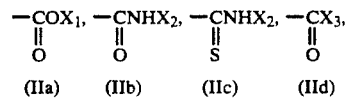

(IIa)  (IIb)  (IIc)  (IId)

$X_1$ is hydrogen, $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, hydroxy, methoxy or/and by ethoxy, $C_7$-$C_{10}$phenylalkyl or $C_7$-$C_{10}$phenylalkyl substituted in the phenyl radical by $C_1$-$C_{20}$alkyl, chlorine, hydroxy, methoxy or/and by ethoxy, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is a group of formula IIIb to IIIg

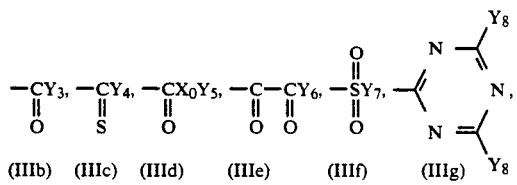

(IIIb) (IIIc) (IIId) (IIIe) (IIIf) (IIIg)

$X_0$ is an oxygen atom or a sulfur atom, $Y_3$ is $C_4$-$C_{20}$alkyl, $C_3$-$C_{20}$alkenyl, phenyl, phenyl substituted by $C_1$-$C_4$alkyl, chlorine, —$NO_2$, methoxy or/and by ethoxy, 2-phenylethenyl, di($C_1$-$C_4$alkyl)amino, diphenylamino, $C_1$-$C_{20}$alkylamino, $C_3$-$C_8$cycloalkylamino, phenylamino, phenylamino substituted in the phenyl ring by $C_1$-$C_4$alkyl, chlorine, hydroxy, methoxy or/and by ethoxy, benzylamino, benzenesulfonamido or toluenesulfonamido, $Y_4$ is di($C_1$-$C_4$alkyl)amino, diphenylamino, $C_1$-$C_8$alkylamino, phenylamino, phenylamino substituted in the phenyl ring by $C_1$-$C_4$alkyl, chlorine, hydroxy, methoxy or/and by ethoxy, or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, or $C_7$-$C_{10}$phenylalkyl substituted in the phenyl radical by $C_1$-$C_2$₀alkyl, $Y_6$ is $C_1$-$C_4$alkoxy, phenylamino or phenylamino substituted in the phenyl group by $C_1$-$C_4$alkyl, chlorine, hydroxy, methoxy or/and by ethoxy, $Y_7$ is $C_1$-$C_4$alkyl, phenyl or phenyl substituted by $C_1$-$C_4$alkyl, chlorine, —$NO_2$, ($C_1$-$C_{12}$alkyl)oxycarbonyl and/or by phenoxycarbonyl, the radicals $Y_8$ are each independently of the other $C_1$-$C_4$alkoxy or allyloxy, and when n is 2 $R_3$ is a group of formula IVa, IVb, IVc or IVd

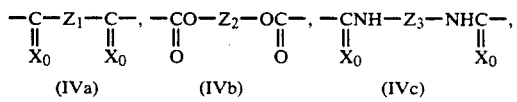

(IVa) (IVb) (IVc)

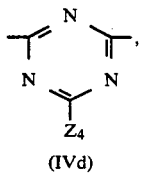

(IVd)

$X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

16. Compounds according to claim 15, wherein n is 1 or 2, $R_1$ is $C_1$-$C_4$alkyl, $R_2$ is a group of formula IIa, IIb, IIc or IId, $X_1$ is $C_1$-$C_{20}$alkyl, $C_3$-$C_6$alkyl interrupted by one or two oxygen atoms or sulfur atoms or/and substituted by OH, $C_3$-$C_{20}$alkenyl, $C_5$-$C_{12}$cycloalkyl, $C_5$-$C_{12}$cycloalkyl substituted by $C_1$-$C_4$alkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_1$-$C_{20}$alkyl, $X_2$ is phenyl or phenyl substituted by from 1 to 3 radicals, the radicals being selected from the group consisting of $C_1$-$C_4$alkyl, chlorine, hydroxy, methoxy, ethoxy and acetylamino, $X_3$ is $C_1$-$C_8$alkyl or phenyl, when n is 1 $R_3$ is a group of formula IIIb to IIIg, $X_0$ is an oxygen atom, $Y_3$ is $C_4$-$C_{20}$alkyl, $C_3$-$C_{20}$alkenyl, phenyl, phenyl substituted by $C_1$-$C_4$alkyl, chlorine, methoxy or/and by ethoxy, 2-phenylethenyl, di($C_1$-$C_4$alkyl)amino, $C_1$-$C_8$alkylamino, phenylamino, benzylamino, benzenesulfonamido or toluenesulfonamido, $Y_4$ is di($C_1$-$C_4$alkyl)amino, $C_1$-$C_8$alkylamino, phenylamino or benzylamino, $Y_5$ is $C_1$-$C_{20}$alkyl, $C_3$-$C_6$alkyl interrupted by one or two oxygen atoms, $C_5$-$C_{12}$cycloalkyl, $C_5$-$C_{12}$cycloalkyl substituted by $C_1$-$C_4$alkyl, phenyl, or $C_7$-$C_{10}$phenylalkyl substituted in the phenyl radical by $C_1$-$C_2$₀alkyl, $Y_6$ is $C_1$-$C_4$alkoxy, phenylamino or phenylamino substituted in the phenyl group by $C_1$-$C_4$alkyl, chlorine, methoxy or/and by ethoxy, $Y_7$ is phenyl or tolyl, the radicals $Y_8$ are each independently of the other $C_1$-$C_4$alkoxy or allyloxy, and when n is 2 $R_3$ is a group of formula IVa, IVb, IVc or IVd, $X_0$ is as defined above, $Z_1$ is a direct bond, $C_1$-$C_{12}$alkylene or phenylene, $Z_2$ is $C_2$-$C_{12}$alkylene or 3-oxapentylene, $Z_3$ is $C_4$-$C_8$alkylene or phenylene and $Z_4$ is $C_1$-$C_4$alkoxy or allyloxy.

17. Compounds according to claim 15, wherein $X_1$ is $C_1$-$C_{18}$alkyl, $C_3$-$C_6$alkyl interrupted by one or two oxygen atoms or sulfur atoms or/and substitued by OH, allyl, methallyl, oleyl, $C_5$-$C_8$cycloalkyl, phenyl, phenyl substituted by $C_1$-$C_{10}$alkyl, chlorine, methoxy or/and by ethoxy, $C_7$-$C_{10}$phenylalkyl or $C_7$-$C_{10}$phenylalkyl substituted in the phenyl radical by $C_8$-$C_{14}$alkyl, $X_3$ is methyl, ethyl or phenyl, $Y_3$ is $C_4$-$C_{18}$alkyl, allyl, methallyl, oleyl, phenyl, phenyl substituted by $C_1$-$C_4$alkyl, chlorine, methoxy or/and by ethoxy, 2-phenylethenyl or di($C_1$-$C_4$alkyl)amino, and $Y_5$ is $C_1$-$C_{18}$alkyl, $C_5$-$C_8$cycloalkyl, phenyl, or $C_7$-$C_{10}$phenylalkyl substituted in the phenyl radical by $C_8$-$C_{14}$alkyl.

18. The compound 2-methyl-3-methoxycarbonyl-4-ethoxycarbonylaminopyrrole, 2-methyl-3-methoxycarbonyl-4-benzoylaminopyrrole, 2-methyl-3-methoxycarbonyl-4-(2',4'-diallyloxy-1',3',5'-triazin-6'-yl)aminopyrrole, 1,4-bis[(2'-methyl-3'-methoxycarbonylpyrrol-4'-yl)carbamoyl]butane or 1,6-bis[(2'-methyl-3'-methoxycarbonylpyrrol-4'-yl)carbamoyloxy]hexane according to claim 15.

* * * * *